(12) United States Patent
Wakitani et al.

(10) Patent No.: US 8,557,536 B2
(45) Date of Patent: Oct. 15, 2013

(54) METHOD OF DETECTING ARTICULAR CARTILAGE DEGENERATION OR DAMAGE

(75) Inventors: Shigeyuki Wakitani, Osaka (JP);
Masashi Nawata, Nagano (JP);
Kyosuke Miyazaki, Tokyo (JP);
Hiroyuki Masuda, Tokyo (JP); Hiroshi Fujita, Tokyo (JP); Yasuhiro Kurahashi, Kanagawa (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 12/525,869

(22) PCT Filed: Feb. 5, 2008

(86) PCT No.: PCT/JP2008/051839
§ 371 (c)(1),
(2), (4) Date: Jun. 9, 2010

(87) PCT Pub. No.: WO2008/096738
PCT Pub. Date: Aug. 14, 2008

(65) Prior Publication Data
US 2011/0151492 A1    Jun. 23, 2011

(30) Foreign Application Priority Data

Feb. 5, 2007 (JP) ................................. 2007-025731

(51) Int. Cl.
*C12Q 1/34* (2006.01)
(52) U.S. Cl.
USPC ................................. 435/18; 435/23; 435/24
(58) Field of Classification Search
USPC ........................................... 435/4, 7.1, 14, 29
See application file for complete search history.

(56) References Cited

U.S. PATENT DOCUMENTS 4,704,356 A * 11/1987 Thonar ........................ 435/7.92

OTHER PUBLICATIONS

Thonar et al., Serum Markers of Systemic Disease Processes in Osteoarthritis, 1995, Journal of Rheumatology, 43: 68-70.*
Tomatsu et al., Keratan sulphate levels in mucopolysaccharidoses and mucolipidoses, 2005, J. Inherit. Metab. Dis. 28(2): 187-202.*
Sakai et al., Pretreatment procedure for the microdetermination of chondroitin sulfate in plasma and urine, 2002, Anal. Biochem. 302(2): 169-74.*
Asari et al., Intra-and extracellular localization of hyaluronic acid and proteoglycan constituents (chondroitin sulfate, keratan sulfate, and protein core) in articular cartilage of rabbit tibia, 1992, Journal of Histochemistry & Cytochemistry 40(11): 1693-1704.*
Toyoda et al., Microdetermination of unsaturated disaccharides produced from chondroitin sulfates in rabbit plasma by high performance liquid chromatography with fluorometric detection, 1988, Anal. Sci. 4: 381-384.*

Thonar, Eugene J-M. A. and Glant Tibor, "Serum Keratan Sulfate—A Marker of Predisposition to Polyarticular Osteoarthritis," Clinical Biochemistry, Jun. 1992, vol. 25, pp. 175-180.
Sweet, M.. Barry E., et al., "Serum Keratan Sulfate Levels in Osteoarthritis Patients," Arthritis and Rheumatism, May 1988, vol. 31, No. 5, pp. 648-652.
Ratcliffe, Anthony, et al., "Differential Levels of Synovial Fluid Aggrecan Aggregate Components in Experimental Osteoarthritis and Joint Disuse," Journal of Orthopaedic Research, 1994, vol. 12, No. 4, pp. 464-473.
Bleasel, Jane F., et al., "Changes in Serum Cartilage Marker Levels Indicate Altered Cartilage Metabolism in Families With the Osteoarthritis-Related Type II Collagen Gene COL2A1 Mutation," Arthritis and Rheumatism, Jan. 1999, vol. 42, No. 1, pp. 39-45.
Wakatani, S., et al., "Serum keratan sulfate is a promising marker of early articular.cartilage breakdown," Rheumatology, Nov. 2007, vol. 46, No. 11, pp. 1652-1656.
Supplementary European Search Report dated Jan. 11, 2010.
Takagishi, Kenji, "Kesseichu Keratan Ryusan Sokuteiho," Clinical Testing, Dec. 1991, vol. 35, No. 13, pp. 1289-1292.
Tanaka, Seisuke, "Marker of Cartilage Catabolism in Serum and Joint Fluid," Japanese Journal of Rheumatism and Joint Surgery, Oct. 20, 1989, vol. VIII, No. 2, pp. 175-176.
Takagishi, Kenji, Yamamoto, Makoto, "Diagnosis of Rheumatoid Arthritis—Using Biochemical technique-, " Japanese Journal of Clinical Medicine, Mar. 1, 1992, vol. 50, No. 3, pp. 490-494.
Yoshihara, Yasuo, Shimmei, Masayuki, "Kansetsu no Seikagakuteki Shindan Marker," Monthly Book Orthopaedics, Sep. 15, 1994, vol. 7, No. 9, pp. 11-20.
Fukuda, Kanji, "Kansetsuen Marker no Kiso to Rinsho Keratan Ryusan," Rheumatology, Jun. 28, 2006, vol. 35, No. 6, pp. 532-536.
Thonar, Eugene J-M. A., et al. "Quantification of Keratan Sulfate in Blood As a Marker of Cartilage Catabolism," Arthritis and Rheumatism, Dec. 1985, vol. 28, No. 12, pp. 1367-1376.
Fife, Rose E., "Identification of Cartilage Matrix Glycoprotein in Synovial Fluid in Human Osteoarthritis," Arthritis and Rheumatism, Apr. 1988, vol. 31, No. 4, pp. 553-556.
Mukai, Naoki, et al., "Soko Fuka ga Nankotsu Taisha Marker ni Oyobosu Eukyo," Dai 20 Kai Journal of the Japanese Orthopaedic Association, Kiso Gakujutsu Shukai Shrokushu, Aug. 25, 2005, vol. 79, No. 8, 2-P6-2, p. S958.

* cited by examiner

*Primary Examiner* — Jon P Weber
*Assistant Examiner* — Robert Yamasaki
(74) *Attorney, Agent, or Firm* — Kratz, Quintos & Hanson, LLP

(57) ABSTRACT

An object of the present invention is to provide a detection method capable of detecting articular cartilage degeneration or damage in which the abnormality cannot be detected in a radiograph in a simple method and with high accuracy, a method of evaluating the rate of progression of articular cartilage degeneration or damage, and the like.
The present invention as a means for achieving the object provides a method of detecting articular cartilage degeneration or damage which cannot be detected in a radiograph, by using the concentration of keratan sulfate in a sample derived from blood as an index, and the like.
Further, the present invention provides a method of evaluating the rate of progression of articular cartilage degeneration or damage by using the concentration of keratan sulfate in a sample derived from blood as an index, and the like.

5 Claims, 1 Drawing Sheet

METHOD OF DETECTING ARTICULAR CARTILAGE DEGENERATION OR DAMAGE

TECHNICAL FIELD

The present invention relates to a method of detecting articular cartilage degeneration or damage which cannot be detected in a radiograph, by using the concentration of keratan sulfate in a sample derived from blood as an index, and the like.

BACKGROUND ART

Among diseases collectively called arthropathy, as a typical disease in which degeneration such as color change, fibrillar feature or fissuring of articular cartilage is caused or articular cartilage is damaged, osteoarthritis such as knee osteoarthritis, hip osteoarthritis and spinal osteoarthritis, and traumatic arthropathy caused by a sport, an accident or the like are exemplified. In the diagnosis of such a disease, plain radiography is generally carried out, and the degree of progression of the disease is diagnosed by evaluating the status of joint space and the presence or absence of osteophyte or the like. However, there are some cases in which individuals complain of arthropathic symptoms such as pain or swelling although an abnormality is not found by plain radiography. Among such cases, by diagnosis through direct visual examination or arthroscopy, there are many cases in which damage to the ligament, tendon or other articular soft tissues is found, and there are cases in which mild degeneration or damage is found on the surface of articular cartilage associated with the tissues.

As described above, if arthroscopy is used, articular cartilage or articular soft tissue degeneration or damage which cannot be detected by radiography can be detected. However, a method using arthroscopy imposes a burden on a patient as compared with in vitro diagnosis and is not a widely used method.

As a component of proteoglycan that forms the extracellular matrix of articular cartilage, keratan sulfate (hereinafter referred to as "KS") is contained, and therefore, an attempt has been made to detect a joint disease by using the KS concentration in blood, synovial fluid or the like as an index.

For example, Miyauchi et al. have proposed a method of detecting a joint disease comprising treating KS in synovial fluid with an enzyme (keratanase II) having an ability to hydrolyze the β-N-acetylglucosaminide linkage and measuring the produced Gal-GlcNAc (6S) (m-ks) by the HPLC method (Patent document 1). However, because in this method, synovial fluid is used as a sample, it is difficult to apply this method to diagnosis of arthropathy such as early knee osteoarthritis and hip osteoarthritis in which accumulation of synovial fluid is not observed.

On the other hand, Thonar et al. have proposed a diagnostic method for an abnormality of cartilage tissue by measuring KS in serum based on the fact that when KS in serum was measured by an immunoassay method using a monoclonal antibody which reacts with KS and the KS concentration in serum was abnormally high in the cases of osteoarthritis, and have also described the serum KS concentration range showing an abnormality of cartilage tissue (Patent document 2). However, in Patent document 2, although it has been disclosed that the KS concentration tends to increase in a blood sample of a patient who has already received treatment of a joint disease, there has been no description or suggestion that articular cartilage degeneration or damage in a stage which cannot be detected in a radiograph can also be detected by measuring the KS concentration in a sample derived from blood. Further, there are many reports published thereafter that the KS concentration in serum is not useful as an index of articular cartilage degeneration. For example, Campion et al. concluded in 1991 from the experimental results of an immunoassay method using a monoclonal antibody which reacts with KS that the KS concentration in serum of a patient with knee osteoarthritis has a low correlation with the clinical symptoms of the patient or radiographic evaluation and the serum KS concentration cannot be used as an index of articular cartilage degeneration (Non-patent document 1).

Patent document 1: JP-A-2001-57900
Patent document 2: JP-B-6-84971
Non-patent document 1: Campion G V. et al., Arthritis Rheum. 1991; 34: 1254-9

DISCLOSURE OF THE INVENTION

Problems to be Solved by the Invention

An object of the present invention is to provide a detection method capable of detecting articular cartilage degeneration or damage in which the abnormality cannot be detected in a radiograph in a simple method and with high accuracy, and the like.

Means for Solving the Problems

The present inventors obtained the consent from test subjects under institutional review board approval and measured the serum KS concentrations not only in patients who were diagnosed as having arthropathy such as osteoarthritis in a radiograph, but also in patients who fell and received a blow to the knee joint during a sport activity such as skiing or soccer to develop cartilage degeneration and were found to have knee articular cartilage degeneration or damage through direct visual examination or arthroscopy and in patients with early knee osteoarthritis, although not found to have articular cartilage degeneration or damage in a radiograph. As a result, it was found that the serum KS concentrations in the patients who were found to have knee articular cartilage degeneration or damage through direct visual examination or arthroscopy although not found to have articular cartilage degeneration or damage in a radiograph were significantly higher than those in the normal subjects. Further, it was also found that the serum KS concentrations tended to be high in the patients who were found to have knee articular cartilage degeneration or damage through arthroscopy although could not be diagnosed as having articular cartilage degeneration or damage in a radiograph as compared with the patients who were diagnosed as having osteoarthritis in a radiograph.

Based on these findings and the like, the present invention provides a method of detecting articular cartilage degeneration or damage which cannot be detected in a radiograph, by using the KS concentration in a sample derived from blood as an index (hereinafter sometimes referred to as "present inventive detection method").

As a preferred embodiment, the present inventive detection method includes the following steps:

Step 1) a step of measuring the KS concentration in a test sample derived from blood; and Step 2) a step of evaluating articular cartilage degeneration or damage which cannot be detected in a radiograph, based on the comparison between the KS concentration measured in Step 1 and the KS concentration in blood of a normal subject.

It is preferred that the KS concentration is measured by a high performance liquid chromatography.

As another embodiment, the present invention provides a method of evaluating the rate of progression of articular cartilage degeneration or damage by using the concentration of keratan sulfate in a sample derived from blood as an index (hereinafter sometimes referred to as "present inventive evaluation method").

Incidentally, the "rate of progression of articular cartilage degeneration or damage" in the present specification is a concept indicating the active degree of progression of articular cartilage degeneration or damage at a certain time point.

As still another embodiment, the present invention provides a method of determining a change in the status over time of articular cartilage degeneration or damage, including at least a step of evaluating the rate of progression of articular cartilage degeneration or damage by the present inventive evaluation method (hereinafter sometimes referred to as "present inventive determination method 1").

As still another embodiment, the present invention provides a method of determining a therapeutic effect on articular cartilage degeneration or damage, including at least a step of comparing the concentration of keratan sulfate in a sample derived from blood collected before treatment and the concentration of keratan sulfate in a test sample derived from blood collected after treatment (hereinafter sometimes referred to as "present inventive determination method 2").

Effect of the Invention

The present inventive detection method can detect articular cartilage degeneration or damage in early stages in which the abnormality cannot be found in a radiograph, and therefore, the method leads to a treatment which aims at improving symptoms or retarding progression of symptoms and is extremely important. The present inventive detection method can be preferably applied also to articular cartilage degeneration or damage accompanied by arthropathy such as osteoarthritis caused by aging, and therefore, the method is extremely important particularly for advanced countries including Japan in which society is aging. Further, there are cases in which secondary osteoarthritis is caused after surgery or the like. In such cases, if articular cartilage degeneration or damage is detected by the present inventive detection method, a treatment which aims at improving symptoms or retarding progression of symptoms can be given, and therefore, the method is extremely useful. Further, the present inventive detection method can also detect articular cartilage degeneration or damage accompanied by traumatic arthropathy such as distortion, bruise or whiplash in a mild stage to such an extent that the abnormality is not found in a radiograph, and therefore, the method is extremely important.

The present inventive evaluation method can be applied to the determination of therapeutic strategy or the like by detecting the rate of progression of articular cartilage degeneration or damage, and can try to improve symptoms, retard progression of symptoms, improve or accomplish health care, and the like, and therefore, the method is extremely useful. Further, by applying the present inventive evaluation method, the present inventive determination method 1 can be provided.

The present inventive determination method 1 can be applied to the prediction of the progress of the pathological status of articular cartilage degeneration or damage, the determination of therapeutic strategy or the like by determining a change in the status over time of articular cartilage degeneration or damage (a change toward deteriorating, remain unchanged, or a change toward healing), and can try to improve symptoms or retard progression of symptoms, and therefore, the method is extremely useful.

The present inventive determination method 2 can be applied to the determination of therapeutic strategy or the like by determining a therapeutic effect on articular cartilage degeneration or damage, and can try to improve symptoms or retard progression of symptoms, and therefore, the method is extremely useful.

Further, the present inventive detection method, the present inventive evaluation method and the present inventive determination methods 1 and 2 can be carried out by using a sample derived from blood which can be easily collected, and therefore, these methods are extremely useful in the orthopedic field.

BEST MODE FOR CARRYING OUT THE INVENTION

Figure 1:
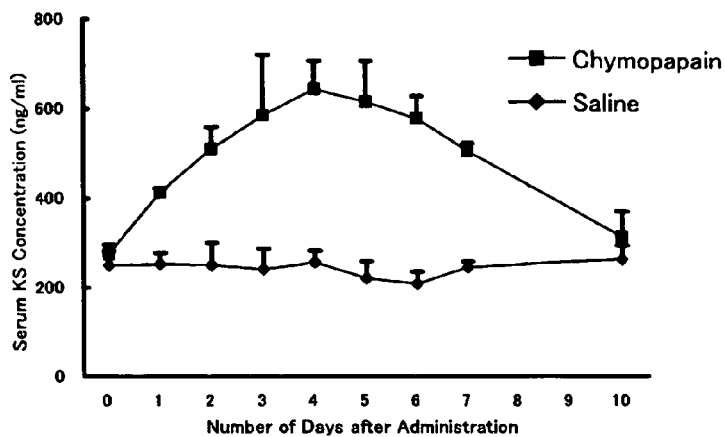
[FIG. 1] A graph showing changes in the serum KS concentrations in rabbit models of arthropathy with the administration of chymopapain and the control.

Hereinafter, the present invention will be described in detail.

1. The Present Inventive Detection Method

The present inventive detection method is a method of detecting articular cartilage degeneration or damage which cannot be detected in a radiograph, by using the concentration of KS in a sample derived from blood (hereinafter referred to as "KS") as an index.

In the above description, the sample derived from blood in which the KS concentration is measured is not particularly limited as long as it enables the measurement of the KS concentration with sufficient accuracy so as to achieve the object of the present inventive detection method. Examples thereof include serum or plasma separated from a blood sample collected by a common blood collection method by removing the other blood components through centrifugation or the like, a fraction extracted from serum or plasma and the like. These can be appropriately selected according to the measurement method described below or the like, however, among these, it is preferred to use serum.

A specific method for carrying out the present inventive detection method is not particularly limited as long as the KS concentration in a sample derived from blood is used as an index, however, for example, the method can be carried out by the following steps:

Step 1) a step of measuring the KS concentration in a test sample derived from blood; and Step 2) a step of evaluating articular cartilage degeneration or damage which cannot be detected in a radiograph, based on the comparison between the KS concentration measured in Step 1 and the KS concentration in blood of a normal subject.

In the above-mentioned Step 1, the method of measuring the KS concentration in a test sample derived from blood is not particularly limited as long as it enables the measurement of the KS concentration with sufficient accuracy so as to achieve the object of the present inventive detection method. For example, a high performance liquid chromatography method (HPLC method), an immunoassay method such as an enzyme-linked immunosorbent assay method (ELISA method) or a radioimmunoassay method, and the like are exemplified. Among these methods, from the viewpoint that a measurement result with higher accuracy is expected to be obtained, it is preferred that the measurement is carried out by HPLC, and particularly, it is more preferred that KS in a sample derived from blood is degraded into KS disaccharides and then the measurement is carried out by HPLC. Incidentally, the HPLC method can be carried out under common conditions by a common procedure.

In particular, for example, in the case where the KS concentration is based on the total amount of β-galactosyl-(1-4)-6-O-sulfo-N-acetylglucosamine (m-ks) and β-6-O-sulfo-galactosyl-(1-4)-6-O-sulfo-N-acetylglucosamine (d-ks) which are obtained by degrading KS in serum into disaccharides by keratanase II which is a KS degrading enzyme, it is preferred that serum digested with a pronase such as actinase is used.

The above-mentioned Miyauchi et al. treated KS by adding keratanase II without performing any pretreatment of synovial fluid and measured the produced disaccharides by the HPLC method. In our study, however, it was found that in the case of using serum as a sample, when KS was treated by adding keratanase II without performing any pretreatment of serum, the degradation ratio thereof was low. Therefore, we conducted various studies in order to increase the degradation ratio of KS in serum by keratanase II, and as a result, it was found that KS was completely degraded when a sample obtained by extracting a KS fraction from serum digested with a pronase such as actinase by using an anion exchange column was used. Accordingly, by degrading KS in a sample derived from blood subjected to such a pretreatment into KS disaccharides and carrying out the measurement by HPLC, articular cartilage degeneration or damage which cannot be detected in a radiograph can be detected with high accuracy.

In the above description, in the case where an immunoassay method is adopted, it is necessary to use an antibody which sufficiently reflects the KS concentration in a sample. For example, Mehmet et al. have reported that the minimum unit structure with which the antibody used in Patent document 2 shows reactivity is a pentasulfated hexasaccharide and further have reported that the antibody does not react with a monosulfated disaccharide, a trisulfated tetrasaccharide or a tetrasulfated hexasaccharide (Eur. J. Biochem., 1986; 157(2): 385-391), however, KS in human serum is rich in low sulfated KS. Therefore, when such an antibody is used for a human serum sample, there is a possibility that the intended KS concentration cannot be accurately measured in the present invention.

In Step 2, articular cartilage degeneration or damage which cannot be detected in a radiograph is evaluated based on the comparison between the KS concentration measured in Step 1 and the KS concentration in blood of a normal subject. The "KS concentration in blood of a normal subject" means the KS concentration in a sample derived from blood of an individual or population who does not complain of arthropathic symptoms. As the above-mentioned "sample derived from blood", serum or plasma separated from a blood sample collected by a common blood collection method by removing the other blood components through centrifugation or the like, a fraction extracted from serum or plasma and the like are exemplified in the same manner as above, however, the sample is preferably the same type of sample as the test sample derived from blood in Step 1. Specifically, in the case where serum is used as a test sample, for example, as the "KS concentration in blood of a normal subject", a mean value of the KS concentrations in sera in the population of normal subjects is used and may be compared with the KS concentration in a sample derived from blood of a subject who is suspected to have articular cartilage degeneration or damage (in the present application document, sometimes referred to as "test sample"). Further, as the "KS concentration in blood of a normal subject", the KS concentration in blood collected in the past (at the time of normal condition) from the subject himself who is suspected to have articular cartilage degeneration or damage can also be used. In this case, since the KS concentration in a test sample can be compared with the past normal KS concentration in the subject himself, it is expected to achieve the evaluation with higher accuracy. Incidentally, the "normal subject" used in the present application document means a subject who does not have arthropathic symptoms, and does not necessarily mean only a subject who does not have any disease.

In the above-mentioned Step 2, in the case where the "KS concentration in a test sample derived from blood" has increased as compared with the "KS concentration in blood of a normal subject", it can be evaluated that the possibility of the presence of articular cartilage degeneration or damage is high. Further, not only the presence or absence of articular cartilage degeneration or damage, but also the degree of articular cartilage degeneration or damage can be evaluated from the degree of increase in the KS concentration. Incidentally, the present inventive detection method is a method in which the measurement of keratan sulfate released from articular cartilage in a progressing stage of articular cartilage degeneration or damage is applied to the detection of articular cartilage degeneration or damage. Accordingly, the "articular cartilage degeneration or damage" in the present inventive detection method can mainly reflect the presence or absence and the degree of progression of articular cartilage degeneration or damage.

In the present inventive detection method, the KS concentration in a sample derived from blood can vary depending on the measurement method or an animal species to which the present inventive detection method is applied, and can be affected also by the presence or absence of other diseases or the like, and therefore cannot be specified in a general manner. However, for example, in the case where serum is used as a sample derived from human blood, the serum KS concentration is based on a value obtained by degrading KS in serum into KS disaccharides and carrying out the measurement by HPLC, and as the serum KS concentration which is evaluated to be the presence of articular cartilage degeneration or damage which cannot be detected in a radiograph, for example, the value of {(the blood KS concentrations in normal subjects)+2×(standard deviation)} or more is exemplified, and as a specific numerical value, for example, a value of preferably about 1200 ng/ml or more, more preferably about 1300 ng/ml or more is exemplified. On the other hand, as the serum KS concentration in a normal subject, a value of about 600 to 1100 ng/ml is exemplified.

The present inventive detection method is characterized by detecting articular cartilage degeneration or damage which cannot be detected in a radiograph. The radiograph used herein means a radiograph obtained by standard X-ray examination to be used in the orthopedic field.

Further, the "articular cartilage degeneration or damage" is not limited by the cause, related disease or the like, however, the present inventive detection method can be more suitably used in the case where articular cartilage degeneration or damage is accompanied by arthropathy such as traumatic arthropathy or osteoarthritis. In the above description, arthropathy is a collective term of joint diseases in which the cartilage, synovial membrane, ligament or the like constituting joint is degenerated or damaged, and which is accompanied by symptoms such as pain, swelling, or fever, and includes osteoarthritis caused by aging and traumatic arthropathy caused by injury.

The "traumatic arthropathy" in the present inventive detection method is not particularly limited by the cause by which it is developed, however, the present inventive detection method can be preferably applied to, for example, the case where the traumatic arthropathy accompanies distortion, bruise, whiplash or the like caused by a sport, an accident or the like. Also, the site is not particularly limited, however, traumatic gonarthrosis or traumatic coxarthropathy are exemplified as a preferred target. The osteoarthritis may be primary osteoarthritis or secondary osteoarthritis caused by injury or in the postoperative course thereof. Specific examples of the osteoarthritis include knee osteoarthritis, hip osteoarthritis and spinal osteoarthritis. The present inventive detection method may be applied to arthropathy in a joint such as an elbow joint or a temporomandibular joint other than the above-mentioned joints, however, from the viewpoint that higher accuracy is expected to be obtained, it is more preferred that the method is applied to arthropathy in a large joint such as a knee joint, a hip joint or an intervertebral disc. Further, from the same reason, the method can be preferably applied also to the case where arthropathy occurs in many sites such as rheumatoid arthritis. Further, the present inventive detection method can also be applied to articular cartilage degeneration or damage accompanied by arthropathy in which a lesion site cannot be specified, for example, as the case of primary osteoarthritis complicating early arthropathy in a joint other than a site with pain or the case of arthropathy without pain symptoms. In such a case, by detecting articular cartilage degeneration or damage by the present inventive detection method and further specifying a lesion site by another method such as MRI or arthroscopy, an early treatment can be initiated. Further, as for traumatic arthropathy, there are many cases in which, although arthropathic symptoms such as pain and swelling are observed in early stages after injury, an abnormality is not found in a radiograph. Therefore, the present inventive detection method can be extremely preferably applied to articular cartilage degeneration or damage accompanied by early traumatic arthropathy. The above-mentioned "early" means, for example, traumatic arthropathy occurring within 2 months after injury. As for such traumatic arthropathy, even if articular cartilage degeneration or damage cannot be detected in a radiograph, if it is evaluated to be arthropathy with articular cartilage degeneration or damage by the present inventive detection method, a treatment can be initiated in early or mild stages. Incidentally, in articular cartilage, there are many cases in which degeneration and damage are simultaneously observed. Therefore, in the present application document, articular cartilage "degeneration or damage" is a concept which also includes the case in which degeneration and damage are simultaneously observed.

Examples of the subject to which the present inventive detection method is applied include mammals such as humans, horses, cattle, sheep, monkeys and dogs, however, among these, humans are preferred.

2. The Present Inventive Evaluation Method

The present inventive evaluation method is a method of evaluating the rate of progression of articular cartilage degeneration or damage by using the KS concentration in a sample derived from blood as an index.

In the present inventive evaluation method, keratan sulfate released from articular cartilage in a progressing stage of articular cartilage degeneration or damage is used as an index, therefore, as the concentration of keratan sulfate in serum is higher, the rate of progression of articular cartilage degeneration or damage is higher, that is, the active degree of progression of articular cartilage degeneration or damage can be determined to be higher.

For the meanings of terms of "sample derived from blood", measurement method of "KS concentration", "subjects to which the method is applied" and the like, please refer to the description of the above-mentioned present inventive detection method.

By the present inventive evaluation method, not only the rate of progression of "articular cartilage degeneration or damage which cannot be detected in a radiograph", but also the rate of progression of "articular cartilage degeneration or damage in grades which can be detected in a radiograph" can be evaluated.

3. The Present Inventive Determination Method 1

The present inventive determination method 1 is a method of determining a change in the status over time of articular cartilage degeneration or damage, including at least a step of evaluating the rate of progression of articular cartilage degeneration or damage by the present inventive evaluation method.

In the above description, the "determining a change in the status over time" means, for example, determining in advance whether the pathological status of articular cartilage degeneration or damage tends to be deteriorated, healed or remain unchanged in future or the like.

More specifically, if the rate of progression of articular cartilage degeneration or damage to be evaluated by the present inventive evaluation method is higher than a reference value, that is, if the active degree of progression of articular cartilage degeneration or damage is higher, the above-mentioned pathological status can be determined that it tends to be deteriorated in future.

On the other hand, if the rate of progression of articular cartilage degeneration or damage to be evaluated by the present inventive evaluation method is lower than a reference value, that is, if the active degree of progression of articular cartilage degeneration or damage is lower, the above-mentioned pathological status can be determined that it tends to be healed or remain unchanged in future.

By the present inventive determination method 1, not only a change in the status over time of "articular cartilage degeneration or damage which cannot be detected in a radiograph", but also a change in the status over time of "articular cartilage degeneration or damage in grades which can be detected in a radiograph" can be determined.

4. The Present Inventive Determination Method 2

The present inventive determination method 2 is a method of determining a therapeutic effect on articular cartilage degeneration or damage, including at least a step of comparing the concentration of keratan sulfate in a sample derived from blood collected before treatment and the concentration of keratan sulfate in a test sample derived from blood collected after treatment.

In the present inventive determination method 2, it is considered that if a patient with arthropathy is treated for arthropathy, and its therapeutic effect is exhibited, the KS concentration in a sample derived from blood after treatment gradually comes closer to the level of a normal subject. Therefore, a therapeutic effect on arthropathy can be determined by using the KS concentration in a sample derived from blood as an index. As the treatment of arthropathy, hyaluronic acid joint injection, administration of any of various drugs such as a nonsteroidal antiinflammatory drug and a steroid, and also exercise therapy, use of a therapeutic instrument such as a therapeutic insole, surgical therapy such as surgery of a joint tissue including articular cartilage, ligament and meniscus, and endoscopic therapy are exemplified.

The sample derived from blood to be used in the above-mentioned determination method, the method of measuring the KS concentration and the like are the same as those in the above-mentioned present inventive diagnostic method. The above-mentioned determination method preferably includes a step of evaluating a therapeutic effect on articular cartilage degeneration or damage which cannot be detected in a radiograph, based on the comparison between the concentration of keratan sulfate in a sample derived from blood collected before treatment and the concentration of keratan sulfate in a test sample derived from blood collected after initiation of treatment.

The "treatment" in the above description means a treatment of articular cartilage degeneration or damage.

By the present inventive determination method 2, not only a therapeutic effect on "articular cartilage degeneration or damage which cannot be detected in a radiograph", but also a therapeutic effect on "articular cartilage degeneration or damage in grades which can be detected in a radiograph" can be determined.

EXAMPLES

Hereinafter, the present invention will be described in more detail with reference to the following Examples, however, the present invention is not limited to the following Examples.

Example 1

Measurement of Serum KS Concentrations after Intraarticular Administration of Chymopapain to Knee Joints of Rabbits Models of arthropathy were produced by administering chymopapain to knee joints of rabbits to cause knee articular cartilage degeneration, and a change in the serum KS concentrations in the models was measured by the HPLC method.

(Method)

Chymopapain (manufactured by Sigma Co., Ltd.) was dissolved at a concentration of 1 mg/mL in physiological saline containing 0.8 mg/mL L-cysteine, and 0.2 mL of the resulting solution was intraarticularly administered to the right hindlimb joints of JW rabbits (body weight: 2.8 to 3.5 kg, n=4). As a control, 0.2 mL of physiological saline was intraarticularly administered to the right hindlimb joints of different JW rabbits (n=4).

Blood was collected from the left ear vein before administration of physiological saline or chymopapain and at 1, 2, 3, 4, 5, 6, 7 and 10 days after the administration, and the serum KS concentration was measured by the HPLC method.

The measurement of the serum KS concentration by the HPLC method was carried out as follows. After 0.8 mL of water was added to 0.2 mL of serum, 0.1 mL of 2% actinase E solution (Kaken Pharmaceutical Co., Ltd.) was added thereto. Then, the resulting solution was let stand at 55° C. for 24 hours and then boiled at 100° C. for 10 minutes. This reaction solution was applied to Q-Sepharose (Amersham Pharmacia Biotech Corp.), and it was washed with 25 mM Tris-HCl buffer (pH 8.6) containing 0.15 M NaCl, and then, KS was extracted with 50 mM Tris-HCl buffer (pH 8.6) containing 2 M NaCl. The thus obtained extracted liquid was desalted by using PD-10 (Amersham Pharmacia Biotech Corp.) and evaporated to dryness under reduced pressure, and the residue was redissolved in 0.2 mL of water. To 0.15 mL of the solution obtained by redissolving the residue, 1 mU keratanase II (Seikagaku Corporation) and 100 mM sodium acetate buffer (pH 6.0) were added, and digestion was performed at 37° C. for 3 hours. The digested liquid was ultrafiltered by using Ultrafree C3GC (Millipore Ltd.), and monosulfated saturated disaccharides (m-ks) and disulfated saturated disaccharides (d-ks) derived from KS contained in the filtrate were quantitatively determined by HPLC. Further, in the confirmation of the ratio of degradation by keratanase II, KS derived from the bovine cornea (Seikagaku Corporation) and KS derived from shark cartilage were used. The conditions of HPLC are as follows.

Column: YMC gel PA-120 (polyamine-bond silica gel, YMC)
Eluent: sodium sulfate/water (0/100→100/0, 45 minutes)
Flow rate: 0.5 mL/min
Detection: Detection was performed with a fluorescence detector (Excitation: 331 nm, Emission: 383 nm) after reaction with 2-cyanoacetamide.

(Result)

Changes in the serum KS concentrations measured in the above are shown in FIG. 1. The serum KS concentrations in the rabbits to which physiological saline was intraarticularly administered to the knee joint did not change between before and after the administration, and remained at about 200 ng/ml. On the other hand, in the group to which chymopapain was intraarticularly administered to the knee joint, the mean serum KS concentration gradually increased and reached the maximum concentration of 643±64 ng/ml at 4 days after the administration, and decreased thereafter and returned to substantially the same level as that of the physiological saline administration group at 10 days after the administration.

The increase in the serum KS concentration is due to the transfer of KS released from knee articular cartilage degenerated by chymopapain to blood, and since KS released from articular cartilage promptly transfers to blood, the detection could be effected by the measurement of KS in the serum sample. Further, since the serum KS concentration returns to the normal level at the time point when articular cartilage degeneration is considered to be subsided, it was shown that the measurement of the serum KS concentration could be used as an index of the status of articular cartilage degeneration or damage.

The following Examples 2 and 3 were carried out under institutional review board (IRB) approval and informed consent from test subjects.

Example 2

Measurement of Serum KS Concentrations in Normal Subjects and Patients with Arthropathy Comparison was made in terms of the serum KS concentrations and arthropathic conditions among 24 normal subjects, 18 patients (TA patients) who visited a hospital due to injury to the knee joint by a sport, bruise or the like and were not found to have an abnormality in a radiograph but were found to have articular cartilage degeneration or damage through direct visual examination or arthroscopy, and 18 patients (OA patients) including patients who visited a hospital for possible knee osteoarthritis and diagnosed as having knee osteoarthritis in a radiograph and patients who were not found to have an abnormality in a radiograph but were found to have articular cartilage degeneration or damage through arthroscopy.

(Method)

The serum KS concentrations were measured in the same manner as in Example 1. The arthropathic conditions were examined by an evaluation of a knee radiograph and arthroscopy. The evaluation of the knee radiograph was carried out according to the method of Kellgren and Lawrence (Ann. Rheum. Dis. 1957, 16, 494-502), and in the evaluation by arthroscopy, SFA (Societe Francaise d'Arthroscopie) was calculated according to the method of Ayral et al. (Osteoarthritis 1998, 494-505).
(Result)

Figure 2:
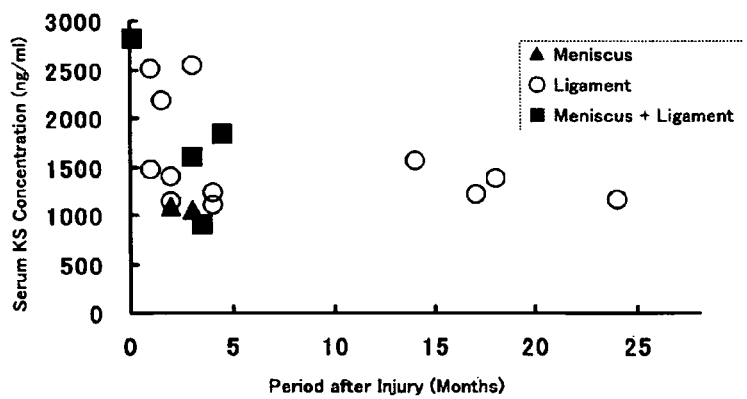
[FIG. 2] A graph showing a relationship between the period after patients with knee injury were injured and the serum KS concentration.
Figure 3:
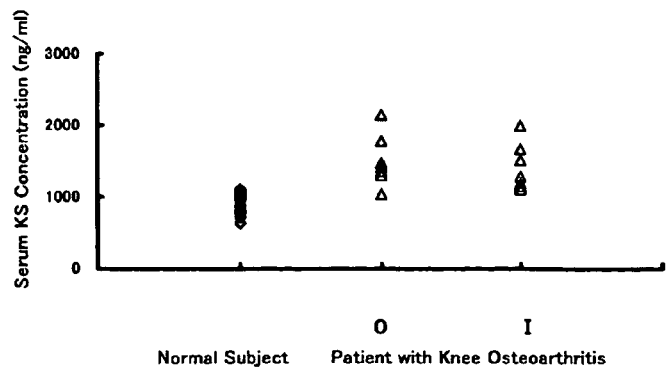
[FIG. 3] A graph showing a distribution of the serum KS concentrations in normal subjects and patients with arthropathy in grades 0 and I.

The above measurement results are shown in Table 1 and FIGS. 2 and 3. Each of the numerical values in Table 1 indicates a mean±a standard deviation. FIG. 2 shows a relationship between the period after the TA patients were injured and the serum KS concentration. FIG. 3 shows the distribution of the serum KS concentrations in the normal subjects and the OA patients in grades 0 and I.

The TA patients showed a mean SFA obtained by arthroscopy of 3.3±3.6 and a serum KS concentration of 1566±574 ng/mL which was significantly higher than that in the normal subjects (910±145 ng/ml) ($p<0.001$). Further, 12 cases among the 18 cases of the TA patients showed a serum KS concentration higher than the value of {(mean value of the serum KS concentrations in the normal subjects)+2×(standard deviation)} (1200 ng/ml). In the case where the period after the TA patients were injured was divided at two months, the patients within two months after injury showed a high serum KS concentration of 2239±577 ng/ml which was significantly higher than that in the TA patients at two months to two years after injury (1373±418 ng/ml). The OA patients also showed a high serum KS concentration, however, a correlation with the results of the evaluation by arthroscopy was not observed, and a tendency to show a high KS concentration in a low grade was observed. The degree of degeneration of articular cartilage of 7 cases among the OA patients who diagnosed as having no abnormality (grade 0) in a radiograph obtained by the evaluation through arthroscopy was substantially identical to the above-mentioned results of the TA patients by arthroscopy. The serum KS concentration in each of these 7 cases was 1501±360 ng/ml, and the number of the cases among these 7 cases showing a higher serum KS concentration than the value of {(mean value of the serum KS concentrations in the normal subjects)+2×(standard deviation)} was 6.

As described above, the serum KS concentrations in both the TA patients and the OA patients are significantly different from those in the normal subjects, and further, in the TA patients, the serum KS concentrations vary depending on the period after injury, and in the OA patients, the serum KS concentrations vary depending on the respective grades, and therefore, it was shown that the serum KS concentration is useful as an index of diagnosis of early arthropathy, determination of grade of arthropathy and the like.

In the measurement of the serum KS concentration by HPLC, m-ks and d-ks obtained by degradation by keratanase II were measured, the ratio of m-ks to d-ks in KS in serum was, for example, about 3.4 in the case of KS in serum of a normal subject. This result shows that blood is rich in low sulfated KS.

Example 3

Measurement of Serum CSDdi6S and COMP Concentrations in Normal Subjects and Patients with Arthropathy The concentrations of a CS-derived unsaturated disaccharide (CSDdi6S) and a cartilage oligomeric matrix protein (COMP) in sera used in Example 2 were measured and compared with the KS concentrations in terms of the usefulness as an index of arthropathy.
(Method)

Specific measurement methods for CSDdi6S and COMP are shown below.
1. CSDdi6S

To 0.2 mL of serum, 0.05 mL of a mixed liquid containing 250 mU chondroitinase ABC (Seikagaku Corporation) and 25 mU chondroitinase AC-II (Seikagaku Corporation), 0.08 mL of 100 mM Tris-HCl buffer (pH 8.0) and 0.07 mL of water were added, and digestion was performed at 37° C. for 2 hours.

The digested liquid was ultrafiltered by using Ultrafree C3GC (Millipore Ltd.), and CSDdi6S contained in the filtrate was analyzed by HPLC. The conditions of HPLC were as follows.
Column: YMC gel PA-120 (polyamine-bond silica gel, YMC)
Eluent: sodium sulfate/water (0/100→100/0, 55 minutes)
Flow rate: 0.5 mL/min
Detection: Detection was performed with a fluorescence detector (Excitation: 346 nm, Emission: 410 nm) after reaction with 2-cyanoacetamide.
2. COMP After 75 μL of a 50-fold or 100-fold dilution of serum was placed in a deep well, 75 μL of an anti-COMP solution was added thereto. After stirring, the well was incubated at 4° C. for 16 hours. As a standard, a COMP solution prepared at a concentration of from 10 ng/mL to 80 ng/mL was treated in the same manner. After incubation, 100 μL of each reaction solution was added to a plate previously immobilized with COMP. After a reaction was allowed to proceed at room temperature for 1 hour, the reaction solution was removed, and each well was washed. 100 μL of a solution of an anti-rabbit IgG labeled with alkaline phosphatase was added to each well, and a reaction was allowed to proceed at room temperature for 1 hour. The reaction solution was removed, and each well was washed. Then, 100 μL of an enzyme substrate solution (pNPP) was added, and a coloring reaction was allowed to proceed at room temperature for 60 minutes. After the reaction, an absorbance at 405 nm was measured within 10 minutes. The concentration of each sample was

TABLE 1

Clinical Diagnosis for Patients with Arthropathy and Concentrations of Serum KS, CSΔdi6S and COMP

|  | Number of test subjects or patients | Period after injury (months) | Evaluation in radiograph (grade) | Evaluation by arthroscopy (SFA) | KS (ng/mL) | CSΔdi6S (ng/mL) | COMP (ng/mL) |
| --- | --- | --- | --- | --- | --- | --- | --- |
| Normal subject | 24 |  |  |  | 910 ± 145 | 97 ± 28 | 1030 ± 150 |
| Patient with knee injury | 4 | <2 | no abnormality | 1.4 ± 0.7 | 2239 ± 577 ***, a | 123 ± 11 | 1590 ± 210 *** |
|  | 14 | 2-24 |  | 3.8 ± 3.9 | 1373 ± 418 *** | 104 ± 22 | 1350 ± 250 *** |
| Patient with knee osteoarthritis | 7 |  | 0 | 2.4 ± 2.1 | 1501 ± 360 *** | 116 ± 18 | 1710 ± 550 *** |
|  | 7 |  | I | 5.1 ± 3.5 | 1411 ± 326 *** | 115 ± 15 | 1570 ± 310 *** |
|  | 4 |  | II | 28.8 ± 47.5 | 1253 ± 241 *** | 102 ± 22 | 1580 ± 200 *** |

** $p < 0.01$,
*** $p < 0.001$ (significant difference with normal subject)
a: $p < 0.01$ (significant difference with patient with knee injury at 2 to 24 months after injury)

obtained by multiplying the measurement concentration calculated from the standard curve by the dilution ratio.

(Result)

The above measurement results are also shown in Table 1. The mean concentrations of CSDdi6S and COMP in sera of the normal subjects were 97 ng/ml and 1030 ng/ml, respectively. In the case of the patients with arthropathy, a significant increase in COMP was observed in the OA and TA patients, however, the increasing rate was lower than that of KS. An increasing tendency was also observed in the case of CSDdi6S, however, an increasing rate thereof was low. As described above, it was confirmed that the usefulness of KS in serum as a marker for early diagnosis of articular cartilage degeneration or damage is higher than that of these substances.

Example 4

Measurement of Serum KS Concentrations in Patients with Arthropathy Before and after Treatment For 24 patients with arthropathy diagnosed as having knee osteoarthritis from clinical observation and a radiograph, comparison was made in terms of a change in the serum KS concentration before treatment and 1 year after initiation of treatment and the presence or absence of progression of arthropathy.

(Method)

The serum KS concentrations were measured in the same manner as in Example 1. Progression of arthropathy was evaluated by plural doctors from knee joint radiographs obtained before treatment and 1 year after initiation of treatment, and the case in which all the doctors participating in the evaluation evaluated that the joint space was narrowed was determined to be "progressive case".

(Result)

Among 24 patients, 5 patients were "progressive cases". In the 5 patients who were "progressive cases", a significant difference in the serum KS concentrations between before and after treatment was not observed. In 19 cases in which the narrowing of the joint space was not observed in the knee joint radiograph 1 year after, the serum KS concentration 1 year after initiation of treatment significantly decreased as compared with that before treatment. Among these 19 cases, the number of the cases in which the KS concentration 1 year after decreased by 30% or more as compared with that before treatment was 7.

As described above, a decrease in the KS concentration was observed in the cases in which progression was not observed in a radiograph and it was confirmed that the measurement of the KS concentration could be applied to the determination of a therapeutic effect.

The invention claimed is:

1. A method of detecting articular cartilage degeneration or damage which cannot be detected in a radiograph, by using a concentration of keratan sulfate in a test sample derived from blood as an index, the method comprising:

extracting a keratan sulfate fraction from serum digested with a pronase, by using an anion exchange column, to obtain a test sample;

degrading keratan sulfate in the test sample into keratan sulfate disaccharide;

measuring the concentration of keratan sulfate in the test sample by measuring a total amount of keratan sulfate disaccharide by high performance liquid chromatography; and evaluating articular cartilage degeneration or damage which cannot be detected in a radiograph, based on a comparison between the concentration of keratan sulfate measured in the test sample and the concentration of keratan sulfate in blood of a normal subject.

2. The detection method according to claim 1, wherein the articular cartilage degeneration or damage is accompanied by arthropathy.

3. The detection method according to claim 2, wherein the arthropathy is traumatic arthropathy or osteoarthritis.

4. The detection method according to claim 3, wherein the arthropathy is traumatic arthropathy occurring within 2 months after injury.

5. The detection method according to claim 2, wherein the arthropathy is arthropathy in a large joint.

* * * * *